United States Patent [19]
Moeckel et al.

[11] Patent Number: 5,955,106
[45] Date of Patent: Sep. 21, 1999

[54] PHARMACEUTICAL PREPARATION CONTAINING METFORMIN AND A PROCESS FOR PRODUCING IT

[76] Inventors: Jörn Moeckel, Am Baechenbuckel 24/1, D-69118 Heidelberg; Rolf-Dieter Gabel, Kurpfalzring 96, D-68723 Schwetzingen; Heinrich Woog, Lindenstrasse 6, D-69514 Laudenbach, all of Germany

[21] Appl. No.: 08/793,753

[22] PCT Filed: Sep. 14, 1995

[86] PCT No.: PCT/EP95/03610

§ 371 Date: Mar. 14, 1997

§ 102(e) Date: Mar. 14, 1997

[87] PCT Pub. No.: WO96/08243

PCT Pub. Date: Mar. 21, 1996

[30] Foreign Application Priority Data

Sep. 14, 1994 [DE] Germany ............................ 44 32 757

[51] Int. Cl.⁶ .................................................... A61K 9/20
[52] U.S. Cl. ........................ 424/464; 424/489; 424/461; 424/480; 424/451
[58] Field of Search .................................. 424/464, 482, 424/466, 480, 489

[56] References Cited

U.S. PATENT DOCUMENTS 4,834,985  5/1989  Elger et al. .............................. 424/488
5,055,306  10/1991  Barry et al. ............................. 424/482

*Primary Examiner*—Thurman K. Page
*Assistant Examiner*—William E. Benston, Jr.

[57] ABSTRACT

The present invention concerns pharmaceutical compositions containing metformin as an active substance and a hydrocolloid-forming agent as a retardant and optionally standard pharmaceutical auxiliary substances, the residual moisture content in the pharmaceutical composition being 0.5–3% by weight. The invention also concerns a process for producing pharmaceutical compositions containing metformin as an active substance and a hydrocolloid-forming agent as a retardant and optionally standard pharmaceutical auxiliary substances characterized in that the active substance and retarding agent or a portion thereof are granulated with an aqueous solvent which can optionally contain a binder and where appropriate the other portion of the retardant or other standard pharmaceutical auxiliaries are admixed with the granulate which is then dried until the residual moisture content is reduced to 0.5–3% by weight.

19 Claims, No Drawings

PHARMACEUTICAL PREPARATION CONTAINING METFORMIN AND A PROCESS FOR PRODUCING IT

The invention concerns pharmaceutical preparations containing metformin hydrochloride (also called metformin in the following) as an active substance and a hydrocolloid-forming agent as a retardant and a process for their production.

It is known that metformin hydrochloride is a biguanide derivative (1,1-dimethylbiguanide monohydrochloride) which has an oral antidiabetic action. Metformin delayed release tablets containing 850 mg metformin hydrochloride per film tablet (Glucophage® retard) are on the market. Since metformin in contrast to other active substances cannot be pressed in its pure form (the mass disintegrates in an unchanged form after the compression) framework-forming auxiliary substances such as polyvinylacetate were used in these high-dose delayed release tablets as a retarding agent (Lipha, technical information Glucophage® August 1991, "Bundesverband der Pharmazeutischen Industrie e.V.", publ. Rote Liste 1993, Edition Cantor, Aulendorf 1993). The mechanism of action of such framework tablets is based on the fact that the readily water-soluble metformin diffuses out of the tablet independently of pH in the gastrointestinal tract whereas the tablet framework with the coating is excreted largely unchanged.

The disadvantage of using such framework-forming auxiliary substances such as polyvinylacetate is, however, that they have to be processed with organic solvents in particular during the granulation process, the organic solvent having to be removed again as completely as possible before the granulate is processed further to compressed pharmaceutical forms of administration and for example pressed into tablets.

The object of the invention was to provide an improved pharmaceutical composition for the active substance metformin. In particular the form of administration should contain the active substance metformin with a highest possible content of active substance and a retardant, the retardant causing a controlled release of the active substance. In particular the new pharmaceutical composition should not contain framework formers which have to be processed with organic solvents but should be composed on the basis of substances that can be processed aqueously. These pharmaceutical compositions should be readily or easily compressible so that they are suitable for the manufacture of solid pharmaceutical forms of administration such as e.g. tablets, dragées or comprimates for filling into capsules. In the case of the manufacture of tablets or other comprimates the maximum total weight should be about 1200–1300 mg in order not to jeopardize the therapeutic safety (patient compliance) since larger oral forms of administration are often not taken in the prescribed regularity.

Another object in the processing of the granulate for these high-dose forms of administration especially in the manufacture of tablets was to solve the problem of capping caused by the active substance which is particularly pronounced in the case of metformin in order to avoid losses of yield during the production and impairment of the pharmaceutical quality. Capping denotes the detachment of compressed mass in layers from the manufactured compact during the pressing or shortly afterwards (Schepky G. in: Bruchhausen, F. von et al.; publ. Hagers Handbuch der pharmazeutischen Praxis, Volume 2, Methoden, 5th ed. "Springer Verlag", Berlin 1991). In the case of metformin and especially when high doses of active substance are present in the granulate it has turned out that the tendency for capping is particularly high during the production of tablets.

The causes for these tabletting problems can be diverse and complex. Capping can be caused by an inadequate binding agent action, an inadequate or excessive moisture content of the granulate, unsuitable crystal forms, strongly aerophilic substances, excessive porosity, excessive proportion of powder, excessive interparticulate binding between the granulate particles and by unsuitable granulate forms. Machine factors which can lead to capping are an excessive pressing force, badly applied or worn tools, excessive pressing rates and poor deaeration of the matrix (fixed pressure). However, in the case of the active substance metformin it has turned out that the usual measures are not adequate to satisfactorily control the capping of the tabletting mass. A relatively high proportion of defective tablets was found during tablet production and the tabletting had to be discontinued due to high reject rates.

In the present case the object of the invention is achieved by providing high-dose pharmaceutical compositions containing metformin which contain a hydrocolloid-forming agent as a retardant and have a residual moisture content in the pharmaceutical composition of 0.5–3% by weight. These pharmaceutical compositions can be advantageously manufactured using aqueous solvents so that organic solvents are no longer required. In addition these compositions are surprisingly easy to compress. They are therefore particularly suitable for the manufacture of solid pharmaceutical forms of administration such as e.g. tablets, dragées or capsules and these can be manufactured with the aid of standard processing machines on a technical scale and in a good quality as well as in a high yield without large losses due to the undesired capping. Accordingly a subject matter of the invention is also a corresponding process for the production of these solid forms of administration in which the appropriate pharmaceutical compositions according to the invention are used in the form of granulates with a residual moisture content of 0.5–3% by weight. The residual moisture content is preferably 1–2.5% by weight in particular 1.5–2% by weight.

Surprisingly it was also found that in the case of the granulate according to the invention it was possible to omit the addition of humectants which are otherwise often necessary to set a constant residual moisture content until the granulate is compressed. This is particularly advantageous because it minimizes the addition of auxiliary substances and pharmaceutical compositions are obtained with a relatively high content of active substance. In addition these compositions have the advantage that they are stable on storage for a period of two days or more (starting from the production up to the use of the granulate for tabletting) with regard to the moisture content before they are compressed without there being a detectable disadvantageous change in the composition. This is particularly advantageous since it enables several partial batches of production lots of the pharmaceutical composition to be produced and these can then be mixed as a mass ready to be pressed at a later time in a common last process step and can be processed to solid pharmaceutical forms of administration.

In addition it surprisingly turned out that the use of a hydrocolloid-forming agent enabled for the first time the known poor compressibility of metformin to be brought under control in a technically satisfactory manner. In addition the solution according to the invention enables the desired retardation and compressibility to be ensured by the selection of the hydrocolloid-forming agent as the retardant and with a suitable control of the production process (adhering to the critical residual moisture content of 0.5–3% by weight in particular of 1–2.5% by weight and 1.5–2% by weight) although the proportion of the hydrocolloid-forming agent in the formulation composition is unusually low. This is even more surprising since the active substance whose water absorbing capacity is very small (the pure active substances only binds 0.04% by weight water at a relative moisture content of 90%) forms the major proportion of the formulation (about 70–95% by weight).

The proportion by weight of the active substance in the high-dose pharmaceutical composition is in the range of at least 70% by weight, preferably 80–95% by weight relative to the pharmaceutical composition. The active substance can be used in the form of acid addition salts of inorganic or organic acids such as e.g. hydrochloric acid, formic acid, acetic acid, malic acid, tartaric acid or furmaric acid. The hydrochloride salt is preferably used.

The proportion of hydrocolloid-forming agent in the pharmaceutical composition is up to 15% by weight preferably 4–10% by weight and especially about 6–8% by weight.

Within the sense of the invention the standard hydrophilic gel forming agents are suitable as hydrocolloid-forming agents or as hydrophilic swelling substances such as for example cellulose derivatives, dextrins, starch, carbohydrate-based polymers, natural or hydrophilic gums, xanthanes, alginates, gelatin, polyacrylic acid, polyvinyl alcohol or polyvinylpyrrolidone. In the case of the cellulose derivatives the alkyl or hydroxyalkyl cellulose derivatives preferably come into consideration such as e.g. methyl cellulose, hydroxymethyl cellulose, hydroxyethyl cellulose, hydroxypropyl cellulose, methylhydroxyethyl cellulose, methylhydroxypropyl cellulose or sodium carboxymethyl cellulose. In a preferred procedural variant of the invention methylhydroxypropyl cellulose (MHPC) is used. The hydrocolloid-forming agents can be used individually as well as in mixtures of two or several colloid-forming agents. The standard polymers suitable for pharmaceutical purposes with various degrees of substitution and/or different molecular weights corresponding to a different degree of viscosity of the aqueous solution can be used as suitable cellulose-based polymeric colloid-forming agents.

The use of hydrocolloid-forming agents as retardants is based on the property of the hydrocolloid-forming agents to swell and form a gel matrix when they are contacted with a release medium or digestive juices which erodes to release the active substance. The interaction between the amount of hydrocolloid-forming agent and the degree of viscosity determines the time course of the release. Thus for example a high proportion (70–95% relative to the core weight of the tablet) of polyvinyl alcohol of a lower or average viscosity level can for example retard riboflavin for several hours (M öckel J. E., Lippold B. C., Pharm. Research, 1993, 10, 1066–1070).

The compressed forms of administration that are produced using the pharmaceutical composition according to the invention such as for example metformin delayed-release tablet cores can be additionally provided with a film envelope. The film envelope can on the one hand cause an additional retardation by using those film materials which represent a film-forming agent which is usually suitable for these purposes. On the other hand the film envelope used can be a taste-neutralizing film-forming agent to which dyes can optionally be added. In addition it is also possible to for example use films that are resistant to gastric juice. The proportion by weight of the film envelope relative to the final tablet is in the usual range of 0.3–3.0% by weight preferably of 0.8–1.2% by weight. Film formers such as for example ethyl cellulose, poly(methylmethacrylate) derivatives (Eudragit®) and also soluble cellulose derivatives such as methylhydroxypropyl cellulose and cellulose derivatives for forming films resistant to gastric juice such as cellulose acetate phthalate or methylhydroxypropyl cellulose phthalate come into consideration as film formers. Ethyl cellulose is preferably used. The dissolution of the active substance can be delayed by the film that is formed. Softeners, pore formers and pigments may be present in the film envelope as standard auxiliary substances.

The pharmaceutical composition according to the invention can also be used to produce compressed capsule filling materials. These comprimates or compacted granulates can then be filled into commercial capsules by means of suitable devices. In comparison to the other standard capsule filling materials containing metformin these compacted granulates have the advantage with the same content of active substance and the same dosage that smaller capsules can be used due to their smaller volume which can be more easily swallowed by the patient.

The pharmaceutical forms of administration according to the invention such as e.g. tablets contain—apart from the active substance whose proportion in the form of administration can be in the range of 70–95% by weight (for example 850 mg of the active substance is preferably used in the case of retarded tablets) and the retardant—preferably 2–10% by weight binder, up to 2% by weight preferably 0.1–0.3% by weight flow regulating agent and up to 2% by weight preferably 0.4–1.1% by weight lubricant each in relation to the total weight of the material ready to be tabletted or of the tablet core. The weight of a tablet core is usually between 200 and 1300 mg preferably in the range of less than 1200 mg especially of about 500–1000 mg. Flow regulating agents which come into consideration for the tablet according to the invention are standard agents such as for example colloidal silicon dioxide. Talcum or stearic acid or alkali or alkaline earth salts thereof in particular magnesium stearate are for example suitable as lubricants. Examples of binding agents that can be used are cellulose derivatives especially alkyl and hydroxyalkyl celluloses in particular methyl cellulose, hydroxymethyl cellulose, hydroxyethyl cellulose, hydroxypropyl cellulose, methylhydroxyethyl cellulose, methylhydroxypropyl cellulose, sodium carboxymethyl cellulose etc., dextrins, starches, especially soluble starches, other polymers based on carbohydrates such as e.g. galactomannans, natural gums such as gum arabic, Traganth, Sterculia, Acacia and others, xanthane, alginates, polyacrylic acid, polyvinyl alcohol and polyvinylpyrrolidone. Polyvinylpyrrolidone is preferably used.

The pharmaceutical forms of administration according to the invention such as e.g. tablets are produced by dry mixing the active substance, the retardant or a portion of the retardant and optionally further auxiliary substances, wet-granulating with water or an aqueous solution of a binder, drying the material ready for tabletting to a desired residual moisture content and subsequently where appropriate the remaining portion of the retardant or other pharmaceutical auxiliary substances are admixed with the granulate so that in the last process step a residual moisture content of 0.5–3% by weight is achieved in the pharmaceutical composition. The determination of the residual moisture content is carried out by known analytical methods of aquametry for example by determining the water content with the aid of the Karl-Fischer reagent or other alternative methods of determination. In the wet granulation a portion of the active substance, the auxiliary substances used as well as the retardant may also be present dissolved or suspended completely or partially in water. Optionally it is also possible to add organic solvents that are miscible with water such as for example acetone or lower alcohols such as methanol or ethanol.

It is expedient to adjust the residual moisture content while drying in a fluid bed process in which the moist granulate is dried until the measured moisture content in the outlet air has reached the value previously determined when the residual moisture content in the drying material was calibrated. The composition produced in this manner is subsequently processed in the usual manner to form pharmaceutical forms of administration and for example pressed into tablets. The tablets can be coated with a film using the standard coating processes. It was found that the residual moisture content of 0.5–3% by weight that was set with the aid of the hydrocolloid-forming agent ensures that the material ready for tabletting can be compressed over the entire range of pressing force required to produce large tablets without capping.

The active substance can be processed completely or partially with the hydrocolloid-forming agent used for the retardation to form a granulate or the hydrocolloid-forming agent is mixed completely with a granulate free of hydrocolloid-forming agent after its production. However, an additional improvement in the tablet-forming properties is achieved when the hydrocolloid-forming agent or a portion thereof is granulated with the active substance.

The tablet is coated by standard methods such as e.g. the coating pan or fluid bed process.

The retarded tablets according to the invention release metformin in a controlled manner over a time period of 0.5–10 hours preferably over 4 hours (FIG. 1). Since due to the use of a hydrocolloid-forming agent large amounts of additional auxiliary substances and in particular no humectants such as for example glycerol or sorbitol are necessary, the maximum weight of the tablets is 1200 mg preferably below 1000 mg.

It is intended to elucidate the invention in the following by the procedural examples without limiting it thereto.

In the following examples 1–6 the residual moisture content was adjusted to the range according to the invention before the pharmaceutical composition in the form of a mass ready for pressing was pressed into tablets. In examples 7 and 8 the residual moisture content was set to a value of less than 0.5% by weight. In these two cases the tabletting had to be terminated due to high losses caused by capping.

EXAMPLE 1

Hydrocolloid-forming agent: methylhydroxypropyl cellulose (MHPC). The MHPC content can be varied e.g. from 40–95 mg.

residual moisture: 2.1%

| Constituents | Tablet [mg] | Mass ready for pressing [kg/1 mio. pieces] |
| --- | --- | --- |
| Core: | | |
| metformin hydrochloride | 850.00 | 850.00 |
| methylhydroxypropyl cellulose | 60.00 | 60.00 |
| polyvidone | 38.00 | 38.00 |
| magnesium stearate | 5.00 | 5.00 |
| core total: | 953.00 | 953.00 |

-continued

| Constituents | Tablet [mg] | Mass ready for pressing [kg/1 mio. pieces] |
| --- | --- | --- |
| Film envelope: | | |
| methylhydroxypropyl cellulose | 20.00 | 20.00 |
| ethyl cellulose | 12.00 | 12.00 |
| Macrogol | 4.00 | 4.00 |
| titanium dioxide | 4.00 | 4.00 |
| envelope total: | 40.00 | 40.00 |
| film tablet total: | 993.00 | 993.00 |

Production

The production of granulate for an amount of about 1 million tablets is carried out in five partial batches. For each of the five partial batches 170 kg metformin hydrochloride and 12 kg methylhydroxypropyl cellulose were dry mixed together and wet-granulated in a mixer with a 10% aqueous binder solution of polyvidone. Subsequently the granulate is dried in a fluid bed granulator until it has an adequate residual moisture content. The five partial batches are combined and admixed with 5 kg magnesium stearate. The mass ready for pressing is tabletted. The tablet cores are coated in a coating pan with the film of the described composition.

In the stated formulation the residual moisture content is adjusted to 2.1%. The tabletting proceeds correspondingly without problems i.e. a capping of the manufactured tablet mass cannot be detected.

EXAMPLE 2

Hydrocolloid-forming agent: hydroxyethyl cellulose

Residual moisture: 2.0%

| Constituents | Tablet [mg] | Mass ready for pressing [kg/1 mio. pieces] |
| --- | --- | --- |
| Core: | | |
| metformin hydrochloride | 850.00 | 850.00 |
| hydroxyethyl cellulose | 70.00 | 70.00 |
| polyvidone | 40.00 | 40.00 |
| magnesium stearate | 5.00 | 5.00 |
| core total: | 965.00 | 965.00 |
| Film envelope: | | |
| methylhydroxypropyl cellulose | 5.00 | 5.00 |
| lactose | 5.00 | 5.00 |
| ethyl cellulose | 10.00 | 10.00 |
| Macrogol | 3.00 | 3.00 |
| titanium dioxide | 3.00 | 3.00 |
| envelope total: | 26.00 | 26.00 |
| film tablet total: | 991.00 | 991.00 |

The granulate is produced and processed analogously to example 1; the tabletting proceeds correspondingly without problems.

EXAMPLE 3

Hydrocolloid-forming agent: sodium carboxymethyl cellulose

Residual moisture: 2.1%

| Constituents | Tablet [mg] | Mass ready for pressing [kg/1 mio. pieces] |
|---|---|---|
| Core: | | |
| metformin hydrochloride | 850.00 | 850.00 |
| sodium carboxy methyl cellulose | 80.00 | 80.00 |
| polyvidone | 35.00 | 35.00 |
| magnesium stearate | 5.00 | 5.00 |
| core total: | 970.00 | 970.00 |
| Film envelope: | | |
| methylhydroxypropyl cellulose | 5.00 | 5.00 |
| ethyl cellulose | 10.00 | 10.00 |
| Macrogol | 4.00 | 4.00 |
| titanium dioxide | 3.00 | 3.00 |
| envelope total: | 22.00 | 22.00 |
| film tablet total: | 992.00 | 992.00 |

The granulate is produced and processed analogously to example 1; the tabletting proceeds correspondingly without problems.

EXAMPLE 4

Hydrocolloid-forming agent: polyacrylic acid

Residual moisture: 2.8%

| Constituents | Tablet [mg] | Mass ready for pressing [kg/1 mio. pieces] |
|---|---|---|
| Core: | | |
| metformin hydrochloride | 850.00 | 850.00 |
| polyacrylic acid | 60.00 | 60.00 |
| methylhydroxypropyl cellulose | 30.00 | 30.00 |
| magnesium stearate | 5.00 | 5.00 |
| core total: | 945.00 | 945.00 |
| Film envelope: | | |
| methylhydroxypropyl cellulose | 10.00 | 10.00 |
| ethyl cellulose | 10.00 | 10.00 |
| Macrogol | 3.00 | 3.00 |
| titanium dioxide | 3.00 | 3.00 |
| envelope total: | 26.00 | 26.00 |
| film tablet total: | 971.00 | 971.00 |

The granulate is produced and processed analogously to example 1. As a variant methylhydroxypropyl cellulose in this case serves as a binder. The tabletting proceeds correspondingly without problems.

EXAMPLE 5

Hydrocolloid-forming agent: hydroxypropyl cellulose

Residual moisture: 1.95%

| Constituents | Tablet [mg] | Mass ready for pressing [kg/1 mio. pieces] |
|---|---|---|
| Core: | | |
| metformin hydrochloride | 850.00 | 850.00 |
| hydroxypropyl cellulose | 60.00 | 60.00 |
| polyvidone | 40.00 | 40.00 |
| magnesium stearate | 5.00 | 5.00 |
| core total: | 955.00 | 955.00 |
| Film envelope: | | |
| poly(ethylacrylate-methyl methacrylate) dispersion 30% | 6.00* | 6.00* |
| talcum | 1.20 | 1.20 |
| anti-foaming agent | 0.07 | 0.07 |
| envelope total: | 7.27 | 7.27 |
| film tablet total: | 962.270 | 962.270 |

*Stated quantity refers to the dry substance.

The granulate is produced and processed analogously to example 1. As a variant the hydrocolloid-forming agent hydroxypropyl cellulose is in this case not granulated simultaneously but admixed dry with the completed granulate.

EXAMPLE 6

Hydrocolloid-forming agent: methylhydroxypropyl cellulose

Residual moisture: 2.0%

In the following example an additional binder is completely omitted, the methylhydroxypropyl cellulose used adopts the function of both binder and retardant.

| Constituents | Tablet [mg] | Mass ready for pressing [kg/1 mio. pieces] |
|---|---|---|
| Core: | | |
| metformin hydrochloride | 850.00 | 850.00 |
| methylhydroxypropyl cellulose | 100.00 | 100.00 |
| magnesium stearate | 5.00 | 5.00 |
| core total: | 955.00 | 955.00 |
| Film envelope: | | |
| methylhydroxypropyl cellulose | 20.00 | 20.00 |
| ethyl cellulose | 12.00 | 12.00 |
| Macrogol | 4.00 | 4.00 |
| titanium dioxide | 4.00 | 4.00 |
| envelope total: | 40.00 | 40.00 |
| film tablet total: | 995.00 | 995.00 |

Production

The production of granulate is carried out in five partial batches. For each of the five partial batches 170 kg metformin hydrochloride and 18 kg methylhydroxypropyl cellulose are placed in a fluid bed granulator. 2 kg methylhydroxypropyl cellulose is dissolved in 50 l water. The dry mixture is granulated with the binder solution in a fluid bed granulator and subsequently dried. The five partial batches are combined and admixed with 5 kg magnesium stearate.

The mass ready for pressing is tabletted. The tablet cores are coated in a coating pan with the film of the described composition.

EXAMPLE 7

Hydrocolloid-forming agent: methylhydroxypropyl cellulose

Residual moisture: 0.49%

A moisture content of 0.49% was obtained with the mixture below. The tabletting had to be stopped due to high losses by capping.

| Constituents | Tablet [mg] |
|---|---|
| Core: | |
| metformin hydrochloride | 850.00 |
| methylhydroxypropyl cellulose | 40.00 |
| polyvidone | 38.00 |
| magnesium stearate | 5.00 |
| core total: | 953.00 |
| film envelope: | |
| methylhydroxypropyl cellulose | 20.00 |
| ethyl cellulose | 12.00 |
| Macrogol | 4.00 |
| titanium dioxide | 4.00 |
| envelope total: | 40.00 |
| film tablet total: | 993.00 |

EXAMPLE 8

Hydrocolloid-forming agent: gelatin

Residual moisture: 0.48%

A moisture of 0.48% was obtained with the mixture below. The tabletting had to be stopped due to high losses by capping.

| Constituents | [mg] |
|---|---|
| Core: | |
| metformin hydrochloride | 850.00 |
| lactose | 70.00 |
| gelatin | 40.00 |
| silicon dioxide, highly dispersed | 2.00 |
| magnesium stearate | 2.50 |
| core total: | 964.50 |
| film envelope: | |
| methylhydroxypropyl cellulose | 10.00 |
| ethyl cellulose | 9.00 |
| diethyl phthalate | 3.00 |
| titanium dioxide | 3.00 |
| envelope total: | 25.00 |
| film tablet total: | 989.5 |

We claim:

1. Pharmaceutical composition comprising metformin as the active substance and a hydrocolloid forming retarding agent, wherein the pharmaceutical composition has a residual moisture content of about 0.5–3% by weight.

2. Composition of claim 1, wherein at least 70% by weight of the composition is metformin.

3. Composition of claim 1, wherein about 4–15% by weight of the composition is the hydrocolloid forming retarding agent.

4. Composition of claim 1, wherein the retarding agent is selected from the group consisting of cellulose derivatives, dextrins, starches, carbohydrate polymers, natural gums, xanthane, alginates, gelatin, polyacrylic acid, polyvinyl alcohol and polyvinyl pyrrolidone.

5. Composition of claim 4, wherein the retarding agent is a cellulose derivative.

6. Composition of claim 5, wherein the cellulose derivative is an alkyl or hydroxyalkyl cellulose.

7. Composition of claim 6, wherein the cellulose derivative is selected from the group consisting of methyl cellulose, hydroxymethyl cellulose, hydroxyethyl cellulose, hydroxypropyl cellulose, methylhydroxyethyl cellulose, methylhydroxypropyl cellulose or sodium carboxymethyl cellulose.

8. Composition of claim 1, further comprising about 3–5% by weight of binder, up to 2% by weight of flow regulating agent and up to 2% by weight of lubricant.

9. Composition of claim 1 in the form of a tablet or capsule.

10. Pharmaceutical tablets or compacted product for filling into capsules comprising metformin as the active substance and a hydrocolloid-forming retarding agent, the tablets having cores, wherein the cores or compacted product have a residual moisture content of about 0.5–3% by weight.

11. Product of claim 10, wherein the product is a tablet having a weight less than 1300 mg.

12. Process for producing a retarded metformin pharmaceutical composition which can be compressed, comprising granulating metformin and a hydrocolloid-forming retarding agent with an aqueous solvent to form a granulated product, and drying the granulated product to a residual moisture content of about 0.5 to 3% by weight.

13. Process of claim 12, including the further step of admixing further retarding agent with the granulated product prior to the drying step.

14. Process of claim 12, wherein the aqueous solvent used in the granulation step contains a binder.

15. Process of claim 12, including the further step of compressing the dried granulated product into tablets.

16. Process of claim 15, including the further step of coating the tablets with a film envelope.

17. Process of claim 12, including the further steps of compacting the dried granulated product to form a compacted product, and filling the compacted product into capsules.

18. Process of claim 12, wherein the retarding agent is methylhydroxypropyl cellulose.

19. Process of claim 12, wherein the compacted product further includes up to 2% by weight of lubricant, up to 2% by weight of flow regulating agent and up to 5% by weight of binder.

* * * * *

US005955106C1

(12) EX PARTE REEXAMINATION CERTIFICATE (6176th)

United States Patent
Moeckel et al.

(10) Number: US 5,955,106 C1
(45) Certificate Issued: Apr. 8, 2008

(54) PHARMACEUTICAL PREPARATION CONTAINING METFORMIN AND A PROCESS FOR PRODUCING IT

(75) Inventors: Jörn Moeckel, Heidelberg (DE); Rolf-Dieter Gabel, Schwetzingen (DE); Heinrich Woog, Laudenbach (DE)

(73) Assignee: Boehringer Mannheim GmbH, Mannheim (DE)

Reexamination Request:
No. 90/006,410, Oct. 7, 2002

Reexamination Certificate for:
Patent No.: 5,955,106
Issued: Sep. 21, 1999
Appl. No.: 08/793,753
Filed: Mar. 14, 1997

(22) PCT Filed: Sep. 14, 1995

(86) PCT No.: PCT/EP95/03610

§ 371 (c)(1),
(2), (4) Date: Mar. 14, 1997

(87) PCT Pub. No.: WO96/08243

PCT Pub. Date: Mar. 21, 1996

(30) Foreign Application Priority Data

Sep. 14, 1994 (DE) .......................... 44 32 757

(51) Int. Cl.
*A61K 9/20* (2006.01)
*A61K 9/14* (2006.01)
*A61K 9/16* (2006.01)
*A61K 9/48* (2006.01)

(52) U.S. Cl. ....................... 424/464; 424/451; 424/461; 424/480; 424/489

(58) Field of Classification Search ........................ None
See application file for complete search history.

(56) References Cited

U.S. PATENT DOCUMENTS

| | | | |
|---|---|---|---|
| 3,174,901 A | 3/1965 | Sterne | |
| 3,490,742 A | 1/1970 | Nichols et al. | ............... 252/99 |
| 3,621,056 A | 11/1971 | Houlihan et al. | ....... 260/545 R |
| 3,621,097 A | 11/1971 | Scott | ........................... 424/247 |
| 3,976,764 A | 8/1976 | Watanabe et al. | ............. 424/19 |
| 4,126,672 A | 11/1978 | Sheth et al. | ................... 424/22 |
| 4,167,558 A | 9/1979 | Sheth et al. | ................... 424/22 |
| 4,207,890 A | 6/1980 | Mamajek et al. | ............ 128/223 |
| 4,248,858 A * | 2/1981 | Guley et al. | ................... 424/21 |
| 4,259,314 A | 3/1981 | Lowey | ........................ 424/129 |
| 4,351,825 A | 9/1982 | Sothmann et al. | |
| 4,357,469 A | 11/1982 | Schor | ........................... 536/91 |
| 4,369,172 A | 1/1983 | Schor et al. | ................... 424/19 |
| 4,434,152 A | 2/1984 | Horvath et al. | ............... 424/19 |
| 4,434,153 A | 2/1984 | Urquhart et al. | .............. 424/22 |
| 4,591,592 A | 5/1986 | Chowhan | |
| 4,704,285 A | 11/1987 | Alderman | ................... 424/468 |
| 4,711,782 A | 12/1987 | Okada et al. | ................. 424/455 |
| 4,767,627 A | 8/1988 | Caldwell et al. | ............. 424/426 |
| 4,792,452 A | 12/1988 | Howard et al. | .............. 424/475 |
| 4,828,836 A | 5/1989 | Elger et al. | ................... 424/419 |
| 4,834,985 A | 5/1989 | Elger et al. | ................... 424/488 |
| 4,844,905 A | 7/1989 | Ichikawa et al. | ............ 424/451 |
| 4,916,163 A | 4/1990 | Ni | ............................... 514/593 |
| 4,954,298 A | 9/1990 | Yamamoto et al. | .......... 264/4.6 |

(Continued)

FOREIGN PATENT DOCUMENTS

| | | |
|---|---|---|
| DE | 27 18 260 | 11/1977 |
| DE | 4414544 A1 | 11/1994 |
| EP | 2 585 948 | 2/1987 |
| EP | 0 283 369 | 9/1988 |
| EP | 0 426 974 | 5/1991 |
| EP | 0502642 A1 | 9/1992 |
| EP | 0 283 369 B1 | 12/1993 |
| EP | 0609961 A1 | 8/1994 |
| EP | 0761209 A3 | 3/1997 |
| FR | 2594693 | 8/1987 |
| GB | 1 527 660 | 10/1978 |
| GB | 1 583 801 | 2/1981 |
| WO | WO 90/11757 | 10/1990 |
| WO | WO 93/18755 | 9/1993 |
| WO | WO 94/27557 | 12/1994 |
| WO | WO 94/27589 | 12/1994 |
| WO | WO 96/31996 | 10/1996 |
| WO | WO 96/32097 | 10/1996 |
| WO | WO 97/18814 | 5/1997 |
| WO | WO 97/35598 | 10/1997 |
| WO | WO 98/11879 | 3/1998 |
| WO | WO 98/55107 | 12/1998 |
| WO | WO 99/30690 | 6/1999 |
| WO | WO 99/47128 | 9/1999 |
| WO | WO 00/35459 | 6/2000 |

(Continued)

OTHER PUBLICATIONS

Notice of Opposition and Opposition to a European Patent filed by Strawman Limited on Mar. 31, 2004.

Notice of Opposition and Opposition from European Patent Office, Dated Apr. 15, 2004, filed by Andrx Corporation (including translation).

(Continued)

*Primary Examiner*—Lakshmi S. Channavajjala

(57) ABSTRACT

The present invention concerns pharmaceutical compositions containing metformin as an active substance and a hydrocolloid-forming agent as a retardant and optionally standard pharmaceutical auxiliary substances, the residual moisture content in the pharmaceutical composition being 0.5–3% by weight. The invention also concerns a process for producing pharmaceutical compositions containing metformin as an active substance and a hydrocolloid-forming agent as a retardant and optionally standard pharmaceutical auxiliary substances characterized in that the active substance and retarding agent or a portion thereof are granulated with an aqueous solvent which can optionally contain a binder and where appropriate the other portion of the retardant or other standard pharmaceutical auxiliaries are admixed with the granulate which is then dried until the residual moisture content is reduced to 0.5–3% by weight.

U.S. PATENT DOCUMENTS

| | | | | |
|---|---|---|---|---|
| 5,007,790 | A | | 4/1991 | Shell .......................... 424/451 |
| 5,030,447 | A | | 7/1991 | Joshi et al. .................... 424/80 |
| 5,055,306 | A | | 10/1991 | Barry et al. ................... 424/482 |
| 5,091,190 | A | | 2/1992 | Kuczynski et al. ......... 424/473 |
| 5,126,145 | A | * | 6/1992 | Evenstad et al. ........... 424/465 |
| 5,169,638 | A | | 12/1992 | Dennis et al. ............... 424/457 |
| 5,232,704 | A | | 8/1993 | Franz et al. ................. 424/456 |
| 5,273,758 | A | | 12/1993 | Royce ......................... 424/465 |
| 5,374,430 | A | | 12/1994 | Newton et al. .............. 424/458 |
| 5,484,608 | A | | 1/1996 | Rudnic et al. ............... 424/468 |
| 5,534,551 | A | | 7/1996 | Page et al. ................... 514/634 |
| 5,545,413 | A | | 8/1996 | Kuczynski et al. ......... 424/473 |
| 5,575,987 | A | | 11/1996 | Kamei et al. ................ 424/451 |
| 5,582,837 | A | | 12/1996 | Shell .......................... 424/451 |
| 5,585,115 | A | | 12/1996 | Sherwood et al. .......... 424/489 |
| 5,591,452 | A | | 1/1997 | Miller et al. ................. 424/468 |
| 5,591,454 | A | | 1/1997 | Kuczynski et al. ......... 424/486 |
| 5,645,858 | A | | 7/1997 | Kotwal et al. ............... 424/495 |
| 5,725,883 | A | | 3/1998 | Staniforth et al. .......... 424/489 |
| 5,824,344 | A | | 10/1998 | Palepu et al. ................ 424/489 |
| 5,955,106 | A | | 9/1999 | Moeckel et al. ............. 424/464 |
| 5,972,389 | A | | 10/1999 | Shell et al. .................. 424/501 |
| 6,031,004 | A | | 2/2000 | Timmins et al. ............. 514/635 |
| 6,099,859 | A | | 8/2000 | Cheng et al. ................ 424/464 |
| 6,099,862 | A | | 8/2000 | Chen et al. .................. 424/473 |
| 6,217,909 | B1 | | 4/2001 | Sherwood et al. .......... 424/494 |
| 6,264,983 | B1 | | 7/2001 | Upadhyay .................... 424/464 |
| 6,284,275 | B1 | | 9/2001 | Chen et al. .................. 424/473 |
| 6,340,475 | B2 | | 1/2002 | Shell et al. .................. 424/469 |
| 6,358,533 | B2 | | 3/2002 | Sherwood et al. .......... 424/494 |
| 2001/0001664 | A1 | | 5/2001 | Sherwood et al. .......... 424/400 |
| 2001/0018070 | A1 | | 8/2001 | Shell et al. .................. 424/469 |

FOREIGN PATENT DOCUMENTS

| | | |
|---|---|---|
| WO | WO 00/57721 | 10/2000 |
| WO | WO 00/57729 | 10/2000 |
| WO | WO 00/59477 | 10/2000 |
| WO | WO 01/07024 A3 | 2/2001 |
| WO | WO 02/28181 A1 | 4/2002 |

OTHER PUBLICATIONS

Povidon, CD Rompp Chemie Lexikon, Version 1.0, Stuttgart/New York; Georg Thieme Verlag 1995 [Povidone, CD Rompp Chemistry—Version 1.0. Stuttgart/New York: Georg Thieme Publishers 1995 (translation of Povidon)].

Vidal 1991, 67th Edition, Editions du Vidal, Entries: Glucidoral, Glucinan, Glucophage, Glucophage Retard, Stagid, and translation.

Repertorio Farmaceutico Italiano, Refi 7th Edizione, 1993, Farmindustria Associazione Nazionale dell'Industria Farmaceutica Entries: Glucophaage, Metforal [Italian Pharmaceutical Index, 7th Edition 1993, Farmindustria National Association of the Pharmaceutical Industry Entries: Glucophage, Metforal (translation of Repertorio Farmaceutico Italiano)].

Antrag auf Verlangerung der Zulassung eines Arzneimittels nach Art. 3 Section 7 des Gesetzes zur Neuordnung des Arznelmittelrechts vom Aug. 24, 1976, BGBI. IS.2445 (AMG 1976) in der geltenden Fassung [Application for Extending the Approval of a Pharmaceutical Product acc. to Art. 3 Section 7 of the Law for the Reorganization of Drug–Related Legislation from Aug. 24, 1976, BGBI (Federal Law Gazette) I P. 2445 (AMG 1976) in the Valid Version (translation of Antrag auf Verlangerung der Zulassung eines Arzneimittels nach Art. 3 Section 7)].

Rote Liste 1993 Arneimittelverzeichnis des BPI, Herausgeber: Bundesverband der Pharmaceutischen Industrie e.V., ECV—Editio Cantor—Aulendorf/Wurtt, (1993), Entry 11081), and full translation.

Anderungsanzeige, Mediabet Tabletten Eing.—Nr. 0608842, Feb. 26, 1993 [Change Notification, Mediabet Tablets, Receipt No. 0608842, dated Feb. 26, 1993 (translation of Anderungsanzeige)].

Preisliste, Stand: May 1, 1993, Medice [Price List, Medice dated May 1, 1993 (translation of Preisliste)].

Prufprotokoll/Freigabe–Zertifikat, Medice, Dated: Apr. 14, 1993 [Test Record/Release Certificate Medice, Dated: Apr. 14, 1993 (translation of Prufprotokoll/Freigabe–Zertifikat)].

Medice Kopie fur Verkauf, dated May 24, 1993 [Medice, Copy for Sales Department, dated May 24, 1993 (translation of Medice Kopie fur Verkauf)].

List, Paul Heinz, Arneiformenlehre: e. Lehrbuch fur Pharmazeuten/von Paul Heinz List. Unter Mitarb. von Bernd :W. Muller u. Eberhard Nurnberg.—2., neubearb. u. erw. Aufli.—Stuttgart: Wissenschaftlich Verlagsgesellschaft, 1980. (ISBN 3–8047–060601) [List, Paul Heinz, Theory of Drug Forms: A Textbook for Pharmacists by Paul Heinz List, with collaboration by Bernd W. Muller and Eberhard Nurnberg. 2nd revised and expanded edition. Stuttgart: Scientific Publication Company, 1980 (translation of List, Paul Heinz, Arneiformenlehre: e. Lehrbuch fur Pharmazeuten/von Paul Heinz List)].

Renewal of Product License, Product License No. 3759/0012–13, dated Mar. 2, 1988.

Hagers Handbuch der Pharmazeutischen Praxis (5th edition) vol. 2, pp. 727–728, Springer, Berlin 1991 [Hager's Handbook of Pharmaceutical Practice, Editor F. von Bruchhausen, 5th edition, vol. 2, Springer–Verlag Berlin Heidelberg 1991 (translation of Hagers Handbuch der Pharmazeutischen Praxis)].

Metformin from the International Drug Directory 1992/93.

Fluka, Catalogue of Chemicals 1997/98 (3 pages).

Lipha, Glucophage/Espagne, dated Jun. 29, 1994, Partie II, Documentation Chimique, Pharmaceutique et Biologique, Jan. 11, 1990 [Lipha, Glucophage Retard, Part II Chemical, Pharmaceutical, and Biological Documentation, Jan. 11, 1990 (translation of Lipha, Glucophage/Espagne)].

Versicherung an Eides statt, dated Mar. 17, 2004 [Affidavit of Bernd Schneider, dated Mar. 17, 2004 (translation of Versicherung an Eides statt)].

Erklarung Dr. Rolf–Dieter Gabel, dated Mar. 25, 2004 [Declaration of Dr. Rolf–Dieter Gabel dated Mar. 25, 2004 (translation of Erklarung Dr. Rolf–Dieter Gabel)].

Erklarung Dr. Heinrich Woog, dated Mar. 23, 2004 [Declaration of Dr. Heinrich Woog, dated Mar. 23, 2004 (translation of Erklarung Dr. Heinrich Woog)].

Erklarung Dr. Joern Moeckel, dated Mar. 23, 2004 [Declaration of Dr. Joern Moeckel, dated Mar. 23, 2004 (translation of Erklarung Dr. Joern Moeckel].

European Patent Application No. 0 781 129; Dated Feb. 4, 2005; Communication from Dr. W. Weiss of Weickmann & Weickmann to Dr. K. Waschbusch at F. Hoffmann–La Roche AG (Original document in German and a translation).

EP Application No. 95 932 741.2 (European Patent No. EP–B–0781129) Decision on Revocation of the European Patent; Dated Jun. 7, 2005 (with translation).

EP Application No. 95 932 741.2 (European Patent No. EP–B–0781129) Minutes of the European Proceedings (with translation), May 18, 2005.

Boraie, et al., "A Study of the Prolonged Release Kinetics of Soluble Drugs from Various Hydrophilic Directly Compressed Cellulosic Matrixes", S.T.P. Pharma (1990), 6(1), 6–12.

Nokhodchi, et al., "An Overview of the Effects of Material and Process Variables on the Compaction and Compression Properties of Hydroxypropoyl Methylcellulose and Ethylcellulose", S.T.P. Pharma Sciences (2001), 11(3), 195–202.

Doelker, E., "Comparative Compaction Properties of Various Microcrystalline Cellulose Types and Generic Products, Drug Development and Industrial Pharmacy", 19(17&18), 2399–2471 (1993).

Chowan, et al., "Compression Properties of Granulations Made with Binders Containing Different Moisture Contents", Journal of Pharmaceutical Sciences vol. 70, No. 10, Oct. 1981.

Rajabi–Siahboomi, et al., "Compression Properties of Methylcellulose and Hydroxpropylmethylcellulose Polymers", Pharm. Pharmacol. Commun. 5, 67–71 (1999).

Lindner, et al., "Controlled Release of Drugs from Hydrocolloid Embeddings", Pharmazie (1996), 51(5), 263–272.

Chaudhuri, et al., "Effect of Water Amount Used During Granulation on Specific Surface and Final Tablet Characteristics", Indian Drugs (1985), 22(9), 476–8.

Cole, et al., "Effect of Moisture Content on the Physical Properties of a Starch Granulation", J. Pharm. Pharmacol. (1975), 27, Suppl. 1P.

Malamataris, et al., "Effect of Particle Size and Sorbed Moisture on the Compression Behaviour of Some Hydroxypropyl Methylcellulose (HPMC) Polymers", Int. J. Pharm., 103, 205–215.

Ghaly, et al., "Effect of Sucralfate on the In–vitro Availability of Some Drugs", Alex. J. Pharm. Sci., vol. 6(1), Feb. 1992.

Staniforth, et al., "Effect of Addition of Water on the Rheological and Mechanical Properties of Microcrystalline Celluloses", International Journal of Pharmaceutics, 41 (1988) 231–236.

Bangudu et al., "Effects of Composition, Moisture and Stearic Acid on the Plasto–elasticity and Tableting of Paracetamol–Microcrystalline Cellulose Mixtures", J. Pharm. Pharmacol. 1985, 37: 289–293.

Timmins, et al., "Evaluation of the Granulation of a Hydrophilic Matrix Sustained–release Tablet", Drug Dev. & Ind. Pharm. (1991), 17(4), 531–50.

Adam, et al., "Factors Influencing Capping and Cracking of Mefenamic Acid Tablets", Drug Development and Industrial Pharmacy, 26(5), 489–497 (2000).

Ragnarsson, et al., "Force–displacement Measurements in Tableting", J. Pharm. Pharmacol. 1985, 37: 145–150.

"Glucovance® (Glyburide and Metformin Hcl Tablets)", Bristol–Myers Squibb Company, Mar. 2001.

Dennis, et al., "In Vitro Comparison of Extended Release pH Independent Matrix Tablets and Capsules", Proc. Int. Symp. Controlled Release Bioact. Mater., 19th (1992), 301–2.

Balan, et al., "In Vitro–in Vivo Correlation (IVIVC) Models for Metformin after Administration of Modified–Release (MR) Oral Dosage Forms to Healthy Human Volunteers", Journal of Pharmaceutical Sciences (2001), 90(8), 1176–1185.

Nyqvist, H., "Influence of Substance Properties on Scaling up of Tablet Formulations", Drug Development and Industrial Pharmacy, 15(6&7), 957–964, 1989.

Timmins, et al., "Influence of Some Process Variables on Product Properties for a Hydrophilic Matrix Controlled Release Tablet", Eur. J. Pharm. Biopharm. 38(3) 113–118 (1992).

Fassihi, A. R., "Interrelationship Between Yield Pressure, Moisture Content and Tensile Strength of Microcrystalline-Cellulose Compacts", Pharmacy & Pharmacology, vol. 40, Supplement, Dec. 1988.

Malamataris, et al., "Moisture Sorption and Tensile Strength of Some Tableted Direct Compression Excipients", International Journal of Pharmaceutics, 68(1991) 51–60.

Chowhan, et al., "Optimization of Tablet Friability, Maximum Attainable Crushing Strength, Weight Variation and In Vitro Dissolution by Establishing In–Process Variable Controls", Drug Development and Industrial Pharmacy, 14(8), 1079–1106 (1988).

Westerhuis, et al., "Optimization of the Composition and Production of Mannitol/Microcrystalline Cellulose Tablets", International Journal of Pharmaceutics (1996), 143(2), 151–162.

Timmins, et al., "Optimization and Characterization of a pH–independent Extended–Release Hydrophilic Matrix Tablet", Pharm. Dev. & Tech. (1997) 2(1), 25–31.

El–Said, Y., "Powder Characteristics, Dissolution Behaviour and Tableting of Acetaminophen Crystallized from Water/Cosolvent Mixtures", Mans. J. Pharm. Sci., vol. 12, No. 2, pp. 237–255, 1996.

Abdallah, et al., "Preparation and Evaluation of Metformin Hydrochloride Controlled–Release Tablets", S.T.P. Pharma 4(1) 15–20 (1988).

Gordon, M.S., "Process Considerations in Reducing Tablet Friability and Their Effect on in Vitro Dissolution", Drug Development and Industrial Pharmacy, 20(1), 11–29 (1994).

Lippold, et al., "Pulsatile Release from Laminated Methylhydroxpropyl Cellulose Matrixes with KCl as Model Drug", Acta Pharm. Technol. (1990), 36(2), 97–8.

Chowhan, et al., "Punch Geometry and Formulation Considerations in Reducing Tablet Friability and Their Effect on in Vitro Dissolution", Journal of Pharmaceutical Sciences, vol. 81, No. 3, Mar. 1992.

Shah, et al., "Some Effects of Humidity and Heat on the Tableting Properties of Microcrystalline Cellulose Formulations I", Journal of Pharmaceutical Sciences, 57, 181 (1968).

Bangudu, A.B., "Some Factors Affecting the Compression Characteristics of Paracetamol Tablets", The Nigerian Journal of Pharmacy, vol. 13, No. 6, Nov.–Dec. 1982.

Nokhodchi, et al., "Studies on the Interaction Between Water and (Hydroxypropyl)methylcellulose", Journal of Pharmaceutical Sciences, vol. 86, No. 5, May 1997.

Ritter, et al., "Studies of Variables That Affect Tablet Capping", Pharmaceutical Technology, Mar. 1980.

Boraie, et al., "Study of the Release Mechanism of a Water Soluble Drug from Hydroxypropylmethylcellulose Matrices", Alex. J. Plharm. Sci., vol. 6(2), Jun. 1992.

Nokhodchi, et al., "The Effect of Moisture on the Compaction Properties of the Binary Mixture of Hydroxypropylmethyl Cellulose K4m/ibuprofen", S.T.P. Pharma Sciences 8(6) 349–356 (1998).

Khan, et al., "The Effect of Moisture on the Density, Compaction and Tensile Strength of Microcrystalline Cellulose", Powder Technol., 54, 161 (1988).

Amidon, et al., "The Effect of Moisture on the Mechanical and Powder Flow Properties of Microcrystalline Cellulose", Pharm. Res. (1995), 12(6), 923–29.

Nyqvist, et al., "The Effect of Water Sorption on Physical Properties of Tablets Containing Microcrystalline Cellulose", Int. J. Pharm. Technol. & Prod. Manuf. (1983), 4(3), 67–73.

Mandal, T., "The Influence of Binding Solvents on Drug Release from Hydroxypropyl Methylcellulose Tablets", Drug Dev. & Ind. Pharm. (1995), 21(12), 1389–97.

Patel, et al., "The Effect of Water Content on Tablet Elastic Recovery", J. Pharm. Pharmacol. (39, Suppl., 11P, 1987) 1 Fig. 3 Ref.

Nokhodchi, et al., "The Influence of Moisture Content on the Consolidation Properties of Hydroxypropylmethylcellulose K4M (HPMC 2008)", Journal of Pharmacy and Pharmacology (1996), 48(11), 1116–1121.

Rees, et al., "The Strength of Compacts Containing Moisture", Pharmaceutica Acta Helvetiae, vol. 47, 234–243 (1972).

Garr, et al., "The Influence of Moisture Content on the Consolidation and Compaction Properties of Paracetamol" International Journal of Pharmaceutics, 81(1992), 187–192.

Esezobo, et al., "The Effects of Moisture Content and Gelatin Binding Agent on the Mechanical and Failure Properties of an Oxytetracycline Formulation", J. Pharm., Pharmac., 1974, 26, Suppl., 47P–56P.

Khan et al., "The Effect of Moisture Content of Microcrystalline Cellulose on the Compressional Properties of Some Formulations", Drug Development and Industrial Pharmacy, 7(5), 525–538 (1981).

Healey, et al., "The Mechanical Properties of Some Binders Used in Tableting", J. Pharm. Pharmac., 1974, 26, Suppl., 41P–46P.

Ford, J. L., "Thermal Analysis of Hydroxypropylmethylcellulose and Methylcellulose: Powders, Gels and Matrix Tablets", International Journal of Pharmaceutics 179 (1999) 209–228.

Moeckel, et al., "Zero–Order Drug Release from Hydrocolloid Matrixes", Pharm. Res. (1993), 10(7), 1066–70.

"Glucophage® (Metformin Hydrochloride Tablets); Glucopohage® XR (Metformin Hydrochloride Extended–Release Tablets)", Bristol–Myers Squibb Company, Jun. 2001.

Barakat, et al., "Extended–Release Verapamil Hydrochloride Tablet Formulation: In–Vitro and In–Vivo Evaluation", Alex. J. Pharm. Sci., vol. 14(1), Mar. 2000.

"Bundesverand der Pharmazeutischen Industrie e.V." publ. Rote Liste 1992, Aulendorf/Wurtt, (1992).

"Bundesverand der Pharmazeutischen Industrie e.V." publ. Rote Liste 1994, Aulendorf/Wurtt (1994), and partial translation.

"Bundesverand der Pharmazeutischen Industrie e.V." publ. Rote Liste 1993, Aulendorf/Wurtt, (1993), and partial translation.

Huttenrach, et al.; Bedeutung des Wassergehalts fur die Tablettierbarkeit verschiedener Starkearten, ein Strukturproblem; Pharmazie 44 (1989), H.11, p. 796–797.

Graf, et al.; "Feststoffdispersionen von Acetohexamid"; Acta Pharmaceutica Technologica 28(3), p. 225–230, (1982).

Arnaud, et al.; "Influence De La Teneur En Humidite Du Granule Sur La Fabrication Et L'Evolution Des Comprimes"; Expo.—Congr. Int. Technol. Pharm., 3rd (1983), vol. 2, 68–78.

DE 4414544 A1; Nov. 10, 1994 (Translation).

FR 2594693; Aug, 28, 1997 (Translation).

Kawashima, Y., et al., "The Effects of Particle Size, Degree of Hydroxypropoxyl Substitution and Moisture Content of Low–Substituted Hydroxypropylcellulose on the Compactibility of Acetaminophen and the Drug Release Rate of the Resultant Tablets", S.T.P. Pharma Sciences 3 (2) 170–177, 1993.

Wenzel, U., et al., "Untersuchungen zum Einfluβ des Trocknungsverlustes von Tablettierhilfsstoffen auf Kraft–Weg–Diagramme und Eigenschaften von Tabletten", Sektion Pharmazie der Martin–Luther–Universitate Halle Wittenberg—Wissenschaftsbereich Pharmazeutische Technologie—(Leiter: OPhRProf. Dr. sc. nat. H. Kala), Pharmazie 39 (1984), H. 12 (pp. 819, 821).

European Patent Application No. 95932741.2—Translation of Response to the communication of oppositions dated May 7, 2004 filed in the Europeant Patent Office (14 pgs).

Lieberman, I., et al., Pharmaceutical Dosage Forms, Tablets:, Marcel Dekker, Inc., 1981 (pp. 181–182) ISBN 0–8247–1269 (v.2).

Cheong, Lucy Wan Sai, et al., "Relationship Between Polymer Viscosity And Drug Release From A Matrix System", Pharmaceutical Research, vol. 9, No. 11, 1992, 1992 Plenum Publishing Corporation (pp. 1510–1514).

Gao, Ping, et al, "Swelling of Hydroxpropyl Methylcellulose Matrix Tablets. 2. Mechanistic Study of the Influence of Formulation Variables on Matrix Performance and Drug Release", Journal of Pharmaceutical Sciences, vol. 85, No. 7, Jul. 1996, 1996, American Chemical Society and American Pharmaceutical Association (pp. 732–740).

Ruggieri, et al., "Studio Delle Caratteristiche Fisiche Delle Compresse AI Variare Della Forza Di Compressione E Dell'Umidita", G. Med. Mil. (1977) 127(3) 246–61.

Seth, et al., "Der Einfluss des Feuchtigkeitsgehaltes Eines Grannulates Auf Die Prefbarkelt Unddie Eigenschaften der Tabletten", Pharmazeutische Technologies; Aus der Galenischen Abteilung des Pharmazeutischen Institutes der ETH, Zurich; 9–12, 1959.

Gibson, Mark, "Pharmaceutical Preformulation and Formulation, A Practical Guide From Candidate Drug Selection to Commerical Dosage Form", Englewood, CO: Interpharm Press 2001, (pp. 398–403).

Robinson, Joseph R., et al., "Controlled Drug Delivery Fundamentals and Applications", Marcel Dekker, Inc., 1987, (pp. 12–36).

Banker, Gilbert S., et al., "Tablet Formulation and Design", Pharmaceutical Dosage Forms, vol. 1, 1980 Marcel Dekker, Inc. (pp. 61–63).

Jetzer, W.E., "Measurement of Hardness and Strength of Tablets and Their Relation to Compaction Performance of Powders", J. Pharm. Pharmacol. 1986, 38: 254–258.

Rowe, Raymond C., "Handbook of Pharmaceutical Excipients", London: Pharmaceutical Press; Washington, D.C.: American Pharmaceutical Association, 2003 (pp. 336–339).

Swarbrick, James, et al., "Encyclopedia Of Pharmaceutical Technology", Microsphere Technology And Applications To Nuclear Magnetic Resonance In Pharmaceutical Technology, vol. 10, Marcel Dekker, Inc., 1988 (pp. 31–65 and 67–82).

European Patent No. 0 781 129 B; Appeal File No. T0951/05–3302; Reply to Statement of Grounds of Appeal, filed Apr. 25, 2006 (18 pgs).

Povidone—Extract from Pharmaceutical Excipients, London: Pharmaceutical Press, Electronic version, (Apr. 2006) (7 pgs) http://www.medicinescomplete.com/mc/excipients/current/1000305948.htm?q=%22pvp%22.

Acacia—Extract from Pharmaceutical Excipients, London: Pharmaceutical Press, Electronic version, (Apr. 2006) (4 pgs), http://www.medicinescomplete.com/mc/excipients/current/1000293171.htm?q=%22arabic%22.

Metformin—The Merck Index, 12th Edition (1996), p. 1014.

Glycine Material Safety Data Sheet; http://www.jtbaker.com/msds/englishhtml/g5828.htm (Apr. 2006) (5 pgs).

Lachman, et al "The Theory and Practice of Industrial Pharmacy", Lea & Febiger 3rd Edition (1986), p. 312.

Alderbom, Goran; "Granule Properties of Importance to Tableting" Acta Pharm. Suec. 25, 229–238, (1988).

Rees, J.E., et al., "The Strength of Compacts Containing Moisture", Pharmaceutica Acta Helvetiae, vol. 47, 235–243 (1972).

Celik, Metin, et al. "An Overview of the Effects of Some Physico–Chemical And Mechanical Characteristics of Particulates on the Compaction and Post–Compaction Properties of Compacts", Drug Development And Industrial Pharmacy, 19 (17 & 18), 2119–2141 (1993).

Dawoodbhai, Shabbir, et al., "The Effect of Moisture on Powder Flow and on Compaction and Physical Stability of Tablets", Drug Development and Industrial Pharmacy, 15(10), 1577–1600 (1989).

Opposition to European Patent No. EP 0781 129 B1; Appeal File No. 0951/05–3.3.2; Response to the Communication dated Oct. 27, 2005; dated Jan. 26, 2006.

Notice of Appeal regarding European Patent No. 0 781 129, dated Jul. 25, 2005 (original document in German).

Notice of Appeal regarding European Patent No. 0 781 129; dated Jul. 25, 2005.

Appeal regarding European Patent No. 0 781 129; dated Oct. 14, 2005 (original document in German).

Appeal regarding European Patent No. 0 781 129; dated Oct. 14, 2005.

Main Motion regarding European Patent No. 0 781 129; dated Oct. 14, 2005.

Main Motion regarding European Patent No. 0 781 129; dated Oct. 14, 2005.

First Auxiliary Motion regarding European Patent No. 0 781 129; dated Oct. 14, 2005 (original document in German).

First Auxiliary Motion regarding European Patent No. 0 781 129; dated Oct. 14, 2005.

Second Auxiliary Motion regarding European Patent No. 0 781 129; dated Oct. 14, 2005 (original document in German).

Second Auxiliary Motion regarding European Patent No. 0 781 129; dated Oct. 14, 2005.

Third Auxiliary Motion regarding European Patent No. 0 781 129; dated Oct. 14, 2005 (original document in German).

Third Auxiliary Motion regarding European Patent No. 0 781 129; dated Oct. 14, 2005.

Fourth Auxiliary Motion regarding European Patent No. 0 781 129; dated Oct. 14, 2005 (original document in German).

Fourth Auxiliary Motion regarding European Patent No. 0 781 129; dated Oct. 14, 2005.

Fifth Auxiliary Motion regarding European Patent No. 0 781 129; dated Oct. 14, 2005 (original document in German).

Fifth Auxiliary Motion regarding European Patent No. 0 781 129; dated Oct. 14, 2005.

Sixth Auxiliary Motion regarding European Patent No. 0 781 129; dated Oct. 14, 2005 (original document in German).

Sixth Auxiliary Motion regarding European Patent No. 0 781 129; dated Oct. 14, 2005.

Letter from Weimer Pharma LLC to Dr. K. Waschbusch dated Oct. 14, 2005 (original document in German).

Letter from Weimer Pharma LLC to Dr. K. Waschbusch dated Oct. 14, 2005.

Extract from the Römpp Chemical Lexica, 9th edition (as referenced on p. 6 of the Appeal) (original document in German).

Extract from the Römpp Chemical Lexica, 9th edition (as referenced on p. 6 of the Appeal).

Answer filed by Merck dated Mar. 3, 2006 (original document in German).

Answer filed by Merck dated Mar. 3, 2006.

WO 96/32097; Oct. 17, 1996 (Translation).

A. Apicella, et al; Poly(ethylene oxide) (PEO) and different molecular weight PEO blends monolithic devices for drug release; Biomaterials 1993. vol. 14 No. 2; pp. 83–90.

Stanely S. Davis, et al; The Effect of Density on the Gastric Cmptying of Single– and Multiple–Unit Dosage Forms; Pharmaceutical Research vol. 3, No. 4, 1986; pp. 208–213.

De Pinho, et al.; Development and biopharmaceutical evaluation of controlled release tablets of metformin hydrochloride using a dissolution medium with gradual pH variation; Rev. Bras. Cienc. Farm. (1999), 35(1), 101–109.

M. P. Gouldson, et al.; "Use of cellulose ether containing excipients with microcrystalline cellulose for the production of pellets containing metformin hydrochloride by the process of extrusion–spheronization"; J. Microencapsulation (1997), 14 (2), 137–153.

J. N. Hunt, et al; "A Relation Between The Chain Length of Fatty Acids and the Slowing of Gastric Emptying"; J Physiol. (1968), 194 pp. 327–336.

P. Karttunen, et al.; "The pharmacokinetics of metformin: a comparison of the properties of a rapid–release and a sustained–release preparation"; International Journal of Cinical Pharmacology, Therapy & Toxicology, vol. 21, No. 1, pp. 31–36.

Mark A. Longer, et al.; "Bioadhesive Polymers as Platforms for Oral Controlled Drug Delivery III: Oral Delivery of Chlorothiazide Using a Bioadhesive Polymer"; Journal of Pharmaceutical Sciences; vol. 74, No. 4, Apr. 1985.

James H. Meyer; "Gastrointestinal Structure and Function on Postcibal Transit of Food and Drug Particles"; Chapter 3, Drug Delivery to the Gastrointestinal Tract; J. G. Hardy et al.; Ellis Harewood, Ltd., Chichester (1989).

M Noel, D.S.; "Kinetic study of normal and sustained release dosage forms of metformin in normal subjects"; Journal of International Biomedical Informational Data, 1980, pp. 9–20.

P. J Pentikalnen; "Bioavailability of metformin. Comparison of solution, rapidly dissolving tablet, and three sustained release products"; *International Journal of Clinical Pharmacology, Therapy and Toxicology*, vol. 24, No. 4—1986, pp. 213–220.

Jacques Timmermans, et al; "Factors Controlling the Bouyancy and Gastric Retention Capabilities of Floating Matrix Capsules: New Data for Reconsidering the Controversy"; *Journal of Pharmaceutical Sciences*, vol. 83, No. 1, Jan. 1994.

N. Vidon; et al.; "Metformin in the digestive tract"; *Diabetes Research and Clinical Practice*, 4 (1988) 223–229.

H. Otayal et al.; "A Dynamical Study of the Compressed Tablet (Part II) The Relationship Between Granule Moisture and Capping" *Ann. Repts. Shionogi Research Lab.* (1954), 1, 462–4 (and translation).

Yasutaka Wada, et al.; "Effects of Adsorbed Water on Compressibility of Powders—The Production Design of Tablet Using Moistened Powder and Its Basic Studies—"; *Yakuzalgaku 50* (2) 215–224 (1990).

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–138 are cancelled.

* * * * *